United States Patent [19]

Rolfe et al.

[11] Patent Number: 5,218,060
[45] Date of Patent: Jun. 8, 1993

[54] CALIXERENE EPOXIDE RESINS AND HARDENERS

[75] Inventors: William M. Rolfe, Haverhill; Michael R. Thoseby, Cambridge, both of England

[73] Assignee: Ciba-Geigy Corporation, Ardsley, N.Y.

[21] Appl. No.: 832,294

[22] Filed: Feb. 7, 1992

[30] Foreign Application Priority Data

Feb. 13, 1991 [GB] United Kingdom ............... 9103041

[51] Int. Cl.$^5$ .................... C08G 8/12; C08G 8/28; C08G 8/32; C08G 8/36
[52] U.S. Cl. .................... 525/507; 528/98; 549/560; 549/559; 549/517; 525/502
[58] Field of Search .............. 528/98; 549/560; 525/507

[56] References Cited

U.S. PATENT DOCUMENTS 4,259,464  3/1981  Buriks et al. ............. 528/144
4,434,265  2/1984  Chasar ..................... 524/339

OTHER PUBLICATIONS

J. B. Niederl et al, J. Am. Chem. Soc. 62, 2512 (1940).

Primary Examiner—John C. Bleutge
Assistant Examiner—Frederick Krass
Attorney, Agent, or Firm—Luther A. R. Hall

[57] ABSTRACT

An epoxide resin having the formula I:

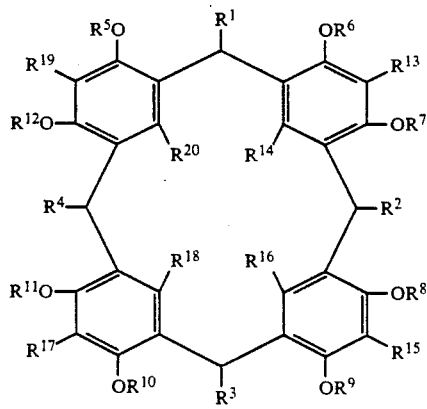

in which $R^1$ to $R^4$ are the same or different and each is hydrogen or $C_1$-$C_{12}$ alkyl; $R^5$ to $R^{12}$ are the same or different and each is $C_1$-$C_{12}$ alkyl or alkenyl or the glycidyl residue such that at least two $R^5$ to $R^{12}$ groups are glycidyl residues; and $R^{13}$ to $R^{20}$ are the same or different and are hydrogen, halogen $C_1$-$C_{12}$ alkyl or alkenyl.

7 Claims, No Drawings

CALIXERENE EPOXIDE RESINS AND HARDENERS

The present invention relates to novel epoxide resins and epoxide hardeners.

In the field of high temperature applications, e.g. castings, fibre-reinforced composites, adhesives and tooling as employed, for instance, in the aerospace industry, there is a constant search for new materials having very high glass transition temperatures (Tg) viz Tgs above 300° C.

The present invention provides epoxide resins having the formula I:

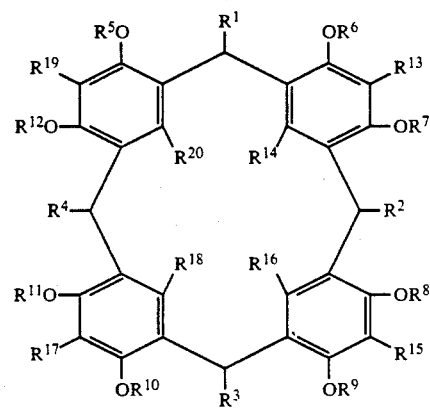

in which $R^1$ to $R^4$ are the same or different, but preferably the same, and each is hydrogen or $C_1$-$C_{12}$ alkyl; $R^5$ to $R^{12}$ are the same or different, and each is $C_1$-$C_{12}$ alkyl or alkenyl or the glycidyl residue.

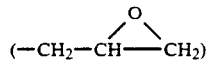

such that at least two such groups are glycidyl residues; and $R^{13}$ to $R^{20}$ are the same or different and are hydrogen, halogen, or $C_1$-$C_{12}$ alkyl or alkenyl.

Alkyl residues $R^1$-$R^{20}$ may be of branched chain or, preferably of straight chain, and may be, e.g. methyl, ethyl, n-propyl, isopropyl, n-butyl, n-pentyl, n-hexyl, n-heptyl, n-octyl, 2-ethylhexyl, n-nonyl, n-decyl, n-undecyl or n-dodecyl.

Alkenyl residues $R^5$ to $R^{20}$ may be, e.g., allyl, methallyl or crotyl.

The new epoxide resins of formula I may be produced by reacting a compound having the formula I in which at least two $R^5$ to $R^{12}$ groups are hydrogen and the remaining $R^5$-$R^{12}$ groups are $C_1$-$C_{12}$ alkyl or alkenyl but all other R groups have their previous significance, with epichlorhydrin under alkaline conditions.

The starting materials of formula I, in which $R_5$ to $R_{20}$ are hydrogen are known, or may be produced by known methods. Niederl and Vogel, J.A.C.S., 1940, 62, 2512, for example, describe the preparation of compounds of formula I in which $R^1$, $R^2$, $R^3$ and $R^4$ are each the same, and each is methyl or ethyl and $R_5$ to $R_{20}$ are all hydrogen.

When cured with a suitable hardener the epoxide resins of formula I provide cured products having very high glass transition temperature (Tg), which products are useful in applications such as castings, fibre-reinforced composites, adhesives, tooling and in high temperature applications such as aerospace uses.

Accordingly, the present invention also provides a heat-curable composition comprising:
1) an epoxide resin of formula (I); and
2) a curing agent for the epoxide resin of formula (I).

The curing agent, component 2), may be one of a great variety of known epoxy curing agents. Examples of suitable curing agents are carboxylic acids or anhydrides such as phthalic anhydride, tetrahydrophthalic anhydride, methyl tetrahydrophthalic anhydride, 5-methylbicyclo[2,2,1]hept-5-ene-2,3-dicarboxylic acid anhydride, pyromellitic dianhydride, trimellitic anhydride, maleic anhydride and dodecenyl succinic anhydride and mixtures thereof; dimer or trimer acids derived from unsaturated fatty acids; Friedel Crafts metal halides, such as aluminum chloride, zinc chloride, boron trifluoride or boron trichloride as well as complexes thereof with ethers, acid anhydrides, ketones and amines; salts such as zinc fluoroborate, magnesium perchlorate and zinc fluorosilicate; aliphatic, aromatic, araliphatic and heterocyclic amino compounds, such as, for example, diethylene triamine, triethylenetetramine, dicyandiamide, melamine, pyridine, benzyldimethylamine, N,N-diethyl-1,3-propanediamine, 4,9-dioxa-1,12-dodecanediamine, dibutylamine, dioctylamine, methylethylamine, pyrrolidine, 2,6-diaminopyridine, 4,4¹-diaminodiphenylmethane and ring-substituted derivatives thereof, 3,3¹- and 4,4¹-diaminodiphenylsulphone, 1,2-, 1,3- and 1,4-phenylenediamines, 2,4-diaminotoluene and ring alkylated derivatives thereof, diaminostilbene, 2,4,6-tris(dimethylaminomethyl) phenol and soluble adducts of amines and poly epoxides and their salts; as well as aromatic diols e.g. resorcinol or hydroquinone or, preferably, di-nuclear aromatic diols e.g. bis (4-hydroxyphenyl) methane (bisphenol F), diallyl bisphenol F, bis (4-hydroxyphenyl) sulphone, 2,2-bis (4-hydroxyphenyl) propane (bisphenol A). The curing agent, component 2) may also be a polyamide containing active amino and/or carboxyl groups, especially one containing a plurality of amino hydrogen atoms and prepared by reacting a polybasic acid with a polyamine.

The curing agent, component 2) may further be a carboxylic acid hydrazide such as stearic acid dihydrazide, oxalic acid dihydrazide, adipic acid dihydrazide, sebacic acid dihydrazide or isophthalic acid dihydrazide; it may also be a 1-cyano-3-alkylguanidine such as 1-cyano-3-methyl guanidine, or the 3,3-dimethyl or 3,3-diethyl derivative; an imidazole such as 2-phenylimidazole, N-methylimidazole or 2-ethyl-4-methyl-imidazole; a salt of a hydroxycarboxylic acid such as lactic acid or salicylic acid, with a tertiary amine such as a Mannich base e.g. 2,4,6-tris(dimethylaminomethyl) phenol; cyanoacetamide; or succinimide.

Component 2) may be also an aminoplast, a phenol formaldehyde resin or a blocked polyisocyanate, the aminoplast or phenol-formaldehyde resin having at least 2 groups of formula

—$CH_2OR$ attached directly to an amidic nitrogen atom or atoms, or directly attached to carbon atoms of a phenolic ring, where R represents a hydrogen atom or an alkyl group from 1 to 6 carbon atoms. Methylolated compounds which can be used include urea-formaldehyde condensates, aminotriazine-formaldehyde condensates, especially melamine-formaldehyde and benzoguanamine-formaldehyde condensates, and phenol-formaldehyde condensates. These may be etherified if desired, e.g. the n-butyl ethers may be used. Examples of suitable blocked polyisocyanates include di-and polyisocyanates blocked with caprolactam, an oxime (e.g. cyclohexanone oxime), a monohydric phenol (e.g. phenol itself, p-cresol, p-t-butylphenol), or a monohydric aliphatic, cycloaliphatic or araliphatic alcohol (e.g. methanol, n-butanol, decanol, 1-phenylethanol, 2-ethoxyethanol and 2-n-butoxyethanol). Suitable isocyanates include aromatic diisocyanates such as 1,3-phenylene-, 1,4-naphthylene-, 2,4- and 2,6-tolylene, and 4,4$^1$-methylene-bis (phenylene) diisocyanate, and also their prepolymers with glycols (e.g. ethylene and propylene glycol), glycerol, trimethylolpropane, pentaerythritol, diethyleneglycol, and adducts of alkylene oxides with these aliphatic polyhydric alcohols.

Preferred curing agents 2) are the above-mentioned aromatic amines or carboxylic acid anhydrides.

The amount of the curing agent component may be varied over a considerable range depending on the curing agent used as is understood by those skilled in the art. Thus, for example, the amine curing agents may be suitably employed in the range of from 1 to 50 parts by weight, per 100 parts by weight of component 1), but where complexes of Friedel Crafts metal halides are used, amounts within the range 0.5 to 10 parts by weight, per 100 parts by weight of component 1) will suffice. Where anhydride curing agents are used, it may be desirable to add a small amount (0.1 to 5 parts by weight, per 100 parts by weight of component 1)) of an accelerator such as a tertiary amine, stannous octoate, sulphide or phosphine, to hasten the cure.

It is well known that polyphenols can be used as hardeners for epoxide resins, but they do not generally provide cured products of very high Tg. Surprisingly, we have found that when a commercial epoxide resin, such as bisphenol A diglycidyl ether, is cured with a compound of formula I in which $R^1$-$R^4$ and $R^{13}$-$R^{20}$ have their previous significance, at least two and not more than seven $R^5$-$R^{12}$ are hydrogen, and the remaining $R^5$-$R^{12}$ groups are $C_1$-$C_{12}$ alkyl or alkenyl residues, then materials with Tgs in excess of 150° C. can be obtained.

Accordingly, the present invention also provides a heat curable composition comprising
a) an epoxide resin of functionality at least 2; and
b) a compound of formula I in which $R^1$ to $R^4$ and $R^{13}$ to $R^{20}$ have their previous significance, at least two and not more seven $R^5$ to $R^{12}$ groups are hydrogen and the remaining $R^5$ to $R^{12}$ groups are $C_1$-$C_{12}$ alkyl or alkenyl residues.

Epoxide resins a) which may be employed in the new composition are preferably those containing at least two groups of formula

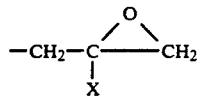

directly attached to an atom of atoms of oxygen, nitrogen, or sulphur, where X denotes a hydrogen atom or a methyl group.

As examples of such resins may be mentioned polyglycidyl and poly(beta-methylglycidyl)esters obtainable by reaction of a compound containing two or more carboxylic acid groups per molecule with epichlorohydrin, glycerol dichlorohydrin, or beta-methylepichlorohydrin in the presence of an alkali. such polyglycidyl esters may be derived from aliphatic polycarboxylic acids, e.g. oxalic acid, succinic acid, glutaric acid, adipic acid, pimelic acid, suberic acid, azelaic acid, sebacic acid, or dimerised or trimerised linoleic acid; from cycloaliphatic polycarboxylic acids such as tetrahydrophthalic acid, 4-methyltetrahydrophthalic acid, hexahydrophthalic acid, and 4-methylhexahydrophthalic acid; and from aromatic polycarboxylic acids such as phthalic acid, isophthalic acid, and terephthalic acid.

Further examples are polyglycidyl and poly(betamethylglycidyl)ethers obtainable by reaction of a compound containing at least two free alcoholic hydroxyl and/or phenolic hydroxyl groups per molecule with the appropriate epichlorohydrin under alkaline conditions or, alternatively, in the presence of an acidic catalyst and subsequent treatment with alkali. These ethers may be made from acrylic alcohols such as ethylene glycol, diethylene glycol, and higher poly(oxyethylene)-glycols, propane-1,2-diol and poly(oxypropylene)-glycols, propane-1,3-diol, butane-1,4-diol, poly(oxytetramethylene)glycols, pentane-1,5-diol, hexane-1,6-diol, hexane-2,4,6-triol, glycerol, 1,1,1-trimethylolpropane, pentaerythritol, sorbitol, and polyepichlorohydrins; from cycloaliphatic alcohols such as resorcitol, quinitol, bis(4-hydroxycylohexyl)methane, 2,2-bis(4-hydroxycyclohexyl)-propane, and 1,1-bis(hydroxymethyl)cyclohex-3-ene; and from alcohols having aromatic nuclei, such as N,N-bis(2-hydroxyethyl)aniline and p,p-bis(2-hydroxyethylamino)diphenylmethane. They may also be made from mononuclear phenols, such as resorcinol and hydroquinone, and from polynuclear phenols, such as bis(4-hydroxyphenyl)methane, 4,4$^1$-dihydroxydiphenyl, bis(4-hydroxyphenyl)sulphone, 1,1,2,2-tetrakis(4-hydroxyphenyl)ethane, 2,2-bis(4-hydroxyphenyl)-propane, 2,2-bis(3,5-dibromo-4-hydroxyphenyl)propane, and novolaks formed from aldehydes such as formaldehyde, acetaldehyde, chloral, and furfuraldehyde, with phenols such as phenol itself, and phenol substituted in the ring by chlorine atoms or alkyl groups each containing up to nine carbon atoms, such as 4-chlorophenyl, 2-methylphenol, and 4-tertbutylphenol.

Poly(N-glycidyl)compounds include, for example, those obtained by dehydrochlorination of the reaction products of epichlorohydrin with amines containing at least two aminohydrogen atoms, such as aniline, n-butylamine, bis(4-aminophenyl)methane, m-xylylenediamine, and bis(4-methylaminophenyl)methane; triglycidyl isocyanurate; and N,N$^1$-diglycidyl derivatives of cyclic alkylene ureas, such as ethyleneurea and 1,3-propyleneurea, and of a hydantion such as 5,5-dimethylhydantoin.

Examples of poly(S-glycidyl) compounds are di-S-glycidyl derivatives of dithiols such as ethane-1,2-dithiol and bis(4-mercaptomethylphenyl)ether.

Epoxide resins having the 1,2-epoxide groups attached to different kinds of hetero-atoms may be employed, e.g. the N,N,O-triglycidyl derivative of 4-aminophenol, the glycidyl ether-glycidyl ester of salicyclic acid, N-glycidyl-N$^1$-(2-glycidyloxypropyl)-5,5-dimethylhydaniton, and 2-glycidyloxy-1,3-bis(5,5-dimethyl-1-glycidylhydantion-3-yl)propane.

If desired, a mixture of epoxide resins may be used. Preferred epoxide resins are liquids, and include polyglycidyl ethers, polyglycidyl esters, N,N¹-diglycidylhydantions, and poly(N-glycidyl) derivatives of aromatic amines. Specific preferred resins are polyglycidyl ethers of 2,2-bis(4-hydroxyphenyl)-propane, of bis(4-hydroxyphenyl)methane, or of a novolak formed from formaldehyde and phenol, or phenol substituted in the ring by one chlorine atom or by one alkyl hydrocarbon group containing from one to nine carbon atoms, and having a 1,2-epoxide content of at least 0.5 equivalent per kilogram, bis(4-(diglycidylamino)phenyl)methane, and p-(diglycidylamino)phenyl glycidyl ether.

The curable compositions may also contain suitable plasticisers such as dibutyl phthalate and dioctyl phthalate, inert diluents such as tars and bitumen and so-called reactive diluents, especially diepoxides such as butane-1,4-diol diglycidyl ether, and diglycidyl ethers of other aliphatic diols, glycidyl ethers of aliphatic polyhydric alcohols, monoepoxides such as n-butyl glycidyl ether, iso-octyl glycidyl ether, phenyl glycidyl ether, cresyl glycidyl ethers, glycidyl esters of mixed tertiary, aliphatic, monocarboxylic acids, glycidyl acrylate, and glycidyl methacrylate. They may also contain additives such as fillers, reinforcing materials, polymeric toughening agents such as polyether sulphones, phenoxy resins, and butadiene-acrylonitrile rubbers, colouring matter, flow control agents, flame inhibitors, and mould lubricants. Suitable extenders, fillers and reinforcing materials are, for example, glass fibres, carbon fibres, fibres of aromatic polyamides, ballotini, mica, quartz flour, calcium carbonate, cellulose, kaolin, wollastonite, colloidal silica having a large specific surface area, powdered poly(vinyl chloride), and powdered polyolefin hydrocarbons such as polyethylene and polypropylene.

The compositions of this invention may be cured by heating them at a suitable temperature, viz. 100° to 300° C., which will vary depending on the nature of the curing agent. The length of the curing process will also vary according to the nature of the curing agent but will range from 15 minutes to one day.

The following Examples further illustrate the present invention.

EXAMPLE 1

2,8,14,20-tetramethylpentacyclo(19,3,1,1$^{3,7}$,1$^{9,13}$,1$^{15,1-9}$)octacosa-1(25)3,5,7(28),9,11,13(27),15,17,19(26),21,23-dodecaene-4,6,10,12,16,18,22,24-octol (68.2 g) is dissolved in 2-methoxyethanol (136.2 g) and epichlorohydrin (370.2 g) added. The mixture is then heated to 60° C. with stirring under nitrogen and a premix of sodium hydroxide (2.0 g), water (3.8 g) and 2-methoxyethanol (2.5 g) added. After 10 minutes solid sodium hydroxide (42.2 g) is added in ten equal portions at 10 minute intervals. The reaction is then maintained at 60° C. for 1 hour and then 1,1,2-trichloroethylene (250 ml) is added, followed by water (184 ml). After separation, the aqueous layer is discarded and the organic layer washed with 10% aqueous sodium dihydrogen phosphate. Solvent is then removed from the organic layer by vacuum distillation at 100° C. to give a very viscous dark brown resin of epoxide content 6.41 mol/kg. (80% of the theoretical value).

EXAMPLE 2

The resin from Example 1 (10 g) is mixed with 5-methylbicyclo(2,2,1)hept-5-ene-2,3-dicarboxylic acid anhydride (9.72 g) and 1-methylimidazole (0.1 g), heated to 150° C. and cast into a mould. This is then heated for 2 hrs at 150° C., 3 hrs. at 180° C. and 4 hrs at 250° C. The resulting cured casting has a T$_g$, measured by Dynamic Mechanical Thermal Analysis, of 338° C.

EXAMPLE 3

The resin from Example 1 (10 g) is mixed with a liquid mixture of 4,4¹-diaminodiphenylmethane, 3-ethyl-4,4¹-diaminodiphenylmethane and 3,3¹-diethyl-4,4¹-diaminodiphenylmethane (3.95 g) and heated to 150° C. and cast into a mould. This is then heated for 2 hrs at 150° C. and cast into a mould. This is then heated for 2 hrs at 150° C., 3 hrs at 180° C. and 4 hrs at 250° C. The resulting cured casting has a T$_g$ of 308° C.

EXAMPLE 4

Example 1 is repeated using 2,8,14,20-tetra-n-propyl-pentacyclo(19,3,1,1$^{3,7}$1,$^{9,13}$,1$^{15,19}$) octacosa-1(25),3,5,7(28),9,11,13(27),15,17,19(26),21,23-dodecaene-4,6,10,12,16,18,22,24-octol (35 g) in place of 2,8,14,20-tetramethylpentacyclo-(19,3,1,1$^{3,7}$,1,$^{9,13}$,1$^{15,19}$) octacosa-1(25),3,5,7(28),9,11,13(27),15,17,19(26),21,23-dodecaene-4,6,10,12,16,18,22,24-octol, 35 ml. of 2-methoxyethanol, 157.8 g of epichlorohydrin and 16.8 g of solid sodium hydroxide. 100 ml. of 1,1,2-trichloroethylene and 72 ml. of water are used in the work up. The resulting very viscous liquid has an epoxy content of 5.24 mol/kg. (72.4% of the theoretical value).

EXAMPLE 5

Example 1 is repeated using 2,8,14,20-tetrapent-1-ylpentacyclo(19,3,1,1$^{3,7}$,1$^{9,13}$,1$^{15,19}$) octacosa-1(25)3,5,7,(28),9,11,13(27),15,17,19(26),21,23-dodecaene-4,6,10,12,16,18,22,24-octol (50 g) in place of 2,8,14,20-tetramethylpentacyclo-(19,3,1,1$^{3,7}$,1$^{9,13}$,1$^{15,19}$) octacosa-1(25)3,5,7(28), 9,11,13(27), 15,17,19(26),21,23-dodecaene-4,6,10,12,16,18,22,24-octol, 80 ml of 2-methoxyethanol, 385 g of epichlorohydrin and 20.9 g of solid sodium hydroxide. 100 ml of 1,1,2-trichloroethylene and 87 ml. of water are used in the work up. The resulting very viscous liquid has an epoxy content of 5.27 mol/kg. (80% of the theoretical value).

EXAMPLE 6

Example 1 is repeated using 2,8,14,20-tetrahept-1-ylpentacyclo(19,3,1,1$^{3,7}$,1$^{9,13}$,1$^{15,19}$) octacosa-1(25)3,5,7(28),9,11,13(27),15,17,19(26),21,23-dodecaene-4,6,10,12,16,18,22,24octol (50 g) in place of 2,8,14,20-tetramethylpentacyclo-(19,3,1,1$^{3,7}$,1$^{9,13}$,1$^{15,19}$) octacosa-1(25)3,5,7(28),9,11,13(27),15,17,19(26),21,23-dodecaene-4,6,10,12,16,18,22,24-octol, 80 ml of 2-methoxyethanol, 168 g of epichlorohydrin and 17.8 g of solid sodium hydroxide. 100 ml. of 1,1,2-trichloroethylene and 76 ml. of water are used in the work up. The resulting very viscous liquid has an epoxy content of 4.68 mol/kg (77% of the theoretical value).

EXAMPLE 7

Example 1 is repeated using 2,8,14,20-tetraundec-1-ylpentacyclo(19,3,1,1$^{3,7}$,1$^{9,13}$,1$^{15,19}$) octacosa-1(25)3,5,7(28),9,11,13(27),15,17,19(26),21,23-dodecaene-4,6,10,12,16,18,22,24-octol (50 g) in place of 2,8,14,20-tetramethylpentacyclo-(19,3,1,1$^{3,7}$,1$^{9,13}$, 1$^{15,19}$) octacosa-1(25)3,5,7(28),9,11,13(27),15,17,19(26),21,23-dodecaene-4,6,10,12,16,18,22,24-octol, 30 ml. of 2-methoxyethanol, 133.9 g of epichlorohydrin and 13.9 g of solid sodium hydroxide. 100 ml of 1,1,2-trichloroethylene and 61 ml of water are used in the work up. The resulting very viscous liquid has an epoxy content of 3.47 mol/kg. (61% of the theoretical value).

EXAMPLE 8

The resin from Example 6 (10 g) is mixed with 5-methylbicyclo(2,2,1)hept-5-ene-2,3-dicarboxylic acid anhydride (5.73 g) and 1-methylimidazole (0.1 g), heated to 150° C. and cast into a mould. This is then heated for 2 hrs at 150° C., 3 hrs at 180° C. and 4 hrs. at 250° C. The resulting cured casting has a $T_g$, measured by Dynamic Mechanical Thermal Analysis, of 347° C.

EXAMPLE 9

Example 1 is repeated using 2,8,14,20-tetraethylpentacyclo(19,3,1,1$^{3,7}$,1$^{9,13}$,1$^{15,19}$) octacosa-1(25)3,5,7,(28),9,11,13(27),15,17,19(26),21,23-dodecaene-4,6,10,12,16,18,22,24-octol (60 g) in place of 2,8,14,20-tetramethylpentacyclo-(19,3,1,1$^{3,7}$,1$^{9,13}$,1$^{15,19}$) octacosa-1(25)3,5,7(28),9,11,13(27),15,17,19(26),21,23-dodecaene-4,6,10,12,16,18,22,24-octol, 50 ml of 2-methoxyethanol, 296.1 g of epichlorohydrin and 33.2 g of solid sodium hydroxide. 200 ml of 1,1,2-trichloroethylene and 148 ml. of water are used in the work up. The resulting very viscous liquid has an epoxy content of 5.68 mol/kg. (75% of the theoretical value).

EXAMPLE 10

The resin from Example 4 (10 g) is mixed with 5-methylbicyclo(2,2,1)hept-5-ene-2,3-dicarboxylic acid anhydride (8.5 g) and 1-methylimidazole (0.1 g), heated to 150° C. and cast into a mould. This is then heated for 2 hrs at 150° C., 3 hrs at 180° C. and 4 hrs. at 250° C. The resulting cured casting has a $T_g$, measured by Dynamic Mechanical Thermal Analysis, of 242° C.

EXAMPLE 11

2-methylresorcinol (100.0 g) and paraformaldehyde (45.2 g) are stirred together in ethanol (400 ml). Concentrated hydrochloric acid is then added, dropwise, with cooling, over fifteen minutes. The mixture is then refluxed until no 2-methylresorcinol is present. The mixture is then filtered and dried at 80° C. to yield the product pentacyclo (19,3,1,1$^{3,7}$,1$^{9,13}$,1$^{15,19}$)octacosa-1(25), 3,5,7 (28),9,11,13(27),15,17,19(26), 21,23-dodecanene-5,11,17,23-tetramethyl-4,6,10,12,16,18,22,24-octol as buff powder with a melting point >300° C.

EXAMPLE 12

The method of Example 1 is repeated using the product from Example 11 (68.2 g), 2-methoxyethanol (136.2 g), epichlorohydrin (370.2 g) and the premix of sodium hydroxide (2.0 g), 2-methoxyethanol (2.5 g) and water (3.8 g), and sodium hydroxide (42.2 g).

The product so obtained has an epoxide content of 6.53 mol kg$^{-1}$ (81% of the theoretical value).

EXAMPLE 13

The product from Example 12 (2.0 g) and 2,2-bis(4-hydroxyphenyl)propane (1.5 g) are melted together at 140° C. for one hour. The mix is cast into small aluminium pans and cured for four hours at 180° C. and a further two hours at 230° C. to give a tough clear casting with a Tg of 270° C. by differential Scanning Calorimetry.

EXAMPLE 14

The product from Example 11 (54.4 g) and potassium carbonate (56.7 g) are slurried together in acetone (300 ml). Methyl iodide (62.4 g) is added dropwise over thirty minutes, keeping the temperature between 15°-20° C. The mixture is then refluxed gently until no starting calix[4]arene is present. The mixture is then filtered and washed with acetone. Solvent is then removed from the filtrate by vacuum distillation at 100° C. to yield the product (52.7 g).

EXAMPLE 15

The method of Example 1 is repeated using the product from Example 14 (50.0 g), epichlorohydrin (128.1 g), 2-methoxyethanol (66.5 g) and the premix of sodium hydroxide (0.7 g), 2-methoxyethanol (1.0 g) and water (1.3 g), and sodium hydroxide (14.0 g).

The product so obtained has an epoxide content of 4.17 mol kg$^{-1}$ (86% of the theoretical value)

EXAMPLE 16

The product from Example 14 (2.0 g) is triple roll milled with Bisphenol A diglycidyl ether (2.52 g), cast into small aluminium pans and cured as in Example 11 to give a brittle casting with a Tg of 152° C. by Differential Scanning Calorimetry.

EXAMPLE 17

The product from Example 15 (2.0 g) and 2,2-bis(4-hydroxyphenyl)propane (0.95 g) are heated together at 160° C. for 20 minutes and cured as in Example 11. The sample gives a brittle casting with a Tg of 133° C.

EXAMPLE 18

The resin from Example 9 (10 g) is mixed with 5-methylbicyclo[2,2,1]hept-5-ene-2,3-dicarboxylic acid anhydride (8.5 g) and 1-methylimidazole (0.1 g), heated to 150° and cast into a mould. This is then heated for 2 hrs at 150° C. and 4 hours at 250° C. The resulting cured casting has a Tg, measured by Dynamic Mechanical Thermal Analysis, of 238° C.

EXAMPLE 19

The resin from Example 9 (10 g) is mixed with a liquid mixture of 4,4$^1$-diaminodiphenylmethane, 3-ethyl-4,4$^1$-diaminodiphenylmethane and 3,3$^1$-diethyl-4,4$^1$-diaminodiphenylmethane (3.2 g) and heated to 150° C. and cast into a mould. This is then heated for 2 hours at 150° C., 3 hours at 180° C. and 4 hours at 250° C. The resulting cured casting has a Tg of 293° C.

We claim:
1. An epoxide resin having the formula I:

in which $R^1$ to $R^4$ are the same or different and each is hydrogen or $C_1-C_{12}$ alkyl; $R^5$ to $R^{12}$ are the same or different and each is $C_1-C_{12}$ alkyl, alkenyl or glycidyl such that at least two $R^5$ to $R^{12}$ groups are glycidyl; and $R^{13}$ to $R^{20}$ are the same or different and are hydrogen, halogen $C_1-C_{12}$ alkyl or alkenyl.

2. A resin according to claim 1 in which $R^1$ to $R^4$ are the same.

3. A resin according to claim 1 in which at least one $R^{13}$ to $R^{20}$ is halogen.

4. A resin according to claim 1 in which at least one $R^{13}$ to $R^{20}$ is a $C_1-C_{12}$ alkyl or alkenyl group.

5. A resin according to claim 1 in which four $R^5$ to $R^{12}$ groups are alkenyl and the other four are glycidyl groups.

6. A resin according to claim 1 in which four $R^5$ to $R^{12}$ are $C_1-C_{12}$ alkyl and the other four are glycidyl groups.

7. A process for the production of an epoxide resin of formula I

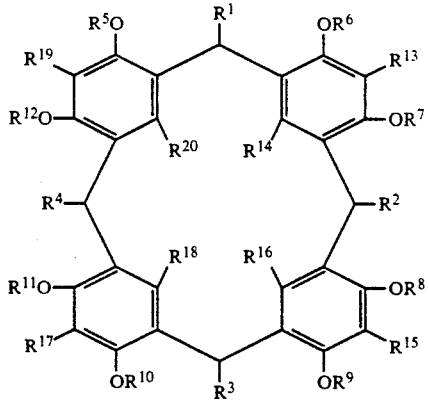

in which
$R^1$ to $R^4$ are the same or different and each is hydrogen or $C_1-C_{12}$alkyl;
$R^5$ to $R^{12}$ are the same or different and each is $C_1-C_{12}$alkyl, alkenyl or glycidyl, such that at least two $R^5$ to $R^{12}$ groups are glycidyl; and
$R^{13}$ to $R^{20}$ are the same or different and are hydrogen, halogen, $C_1-C_{12}$alkyl or alkenyl, comprising
reacting a polyphenol having the structural formula

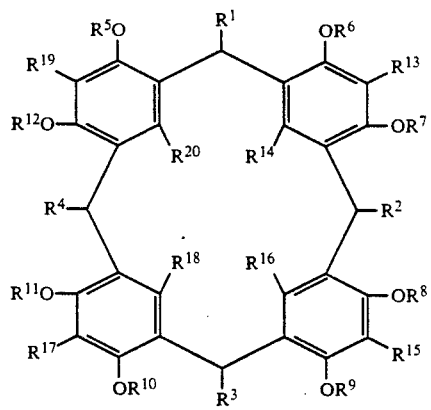

where
at least two $R^5$ to $R^{12}$ groups are hydrogen and the other $R^5$ to $R^{12}$ groups are the same or different and are $C_1-C_{12}$alkyl or alkenyl, and $R^1$ to $R^4$ and $R^{13}$ to $R^{20}$ are as defined above,
with epichlorohydrin under alkaline conditions.

* * * * *